(12) United States Patent
Sayegh

(10) Patent No.: US 9,795,504 B2
(45) Date of Patent: Oct. 24, 2017

(54) EYE FIXATION SYSTEM FOR POSTERIOR AND ANTERIOR SEGMENT EYE SURGERY AND PROCEDURES

(71) Applicant: Samir Sayegh, Champaign, IL (US)

(72) Inventor: Samir Sayegh, Champaign, IL (US)

( * ) Notice: Subject to any disclaimer, the term of this patent is extended or adjusted under 35 U.S.C. 154(b) by 888 days.

(21) Appl. No.: 13/967,063

(22) Filed: Aug. 14, 2013

(65) Prior Publication Data

US 2014/0158139 A1   Jun. 12, 2014

Related U.S. Application Data

(60) Provisional application No. 61/682,770, filed on Aug. 14, 2012.

(51) Int. Cl.
| | |
|---|---|
| *A61F 9/007* | (2006.01) |
| *A61B 17/02* | (2006.01) |
| *A61B 3/00* | (2006.01) |
| *A61B 17/34* | (2006.01) |
| *A61F 9/00* | (2006.01) |

(52) U.S. Cl.
CPC .......... *A61F 9/007* (2013.01); *A61B 17/0231* (2013.01); *A61B 3/00* (2013.01); *A61B 2017/3407* (2013.01); *A61F 2009/0052* (2013.01)

(58) Field of Classification Search
CPC . A61F 9/00; A61F 9/007; A61F 9/013; A61B 17/0231; A61B 3/00
USPC ............................ 128/858; 351/200; 606/166
See application file for complete search history.

(56) References Cited

U.S. PATENT DOCUMENTS

| | | | |
|---|---|---|---|
| 5,951,579 A | 9/1999 | Dykes | |
| 2002/0120285 A1 | 8/2002 | Schachar et al. | |
| 2004/0267294 A1 | 12/2004 | Will | |
| 2005/0288697 A1* | 12/2005 | Tei ..................... | A61B 17/3403 606/166 |
| 2008/0091224 A1* | 4/2008 | Griffis, III ............... | A61F 9/007 606/166 |
| 2013/0060254 A1 | 3/2013 | Juhasz et al. | |

FOREIGN PATENT DOCUMENTS

EP          1099432 A    5/2001

OTHER PUBLICATIONS

Allen C. Ho, Microincision Vitrectomy Surgery Technique Evolves, Ophthalmology Times, Jun. 15, 2011, available at http://ophthalmologytimes.modernmedicine.com/ophthalmologytimes/news/modernmedicine/modern-medicine-feature-articles/microincision-vitrectomy-sur (last retrieved Oct. 21, 2013).
Ashraf M El-Batarny, Transconjunctival Sutureless 23-gauge Vitrectomy for Vitreoretinal Diseases: Outcome of 30 Consecutive Cases, Middle East Afr J Ophthalmol. 15(3): 99-105, Jul.-Dec. 2008, available at http://www.ncbi.nlm.nih.gov/pmc/articles/PMC3040921/ (last visited Oct. 22, 2013).

(Continued)

*Primary Examiner* — Keri J Nelson
(74) *Attorney, Agent, or Firm* — Wendy Thai

(57) ABSTRACT

The invention provides an eye fixation system that allows accurate positioning, stabilization and safe and efficient manipulation of the eye and surgical instrumentation used during procedures and surgeries of the anterior and posterior segments of the eye.

3 Claims, 3 Drawing Sheets

(56) References Cited

OTHER PUBLICATIONS

Helmut Kapczynski, Surgical Instruments 101: An Introduction to KMedic Certified Instruments, 1997, KMedic, Northvale, NJ, available at http://www.teleflex.com/en/usa/pdf/KMedic_Surgical_Instruments_101.pdf (last visited Oct. 22, 2013).
Highlights from the Advanced Vitreoretinal Techniques & Technology Symposium in Hong Kong, Retina Today, Sep./Oct. 2008, available at http://www.retinatoday.com/issues/0908/0908_supp.pdf (last visited Oct. 22, 2013).
Lemley, C.A. & Han, D.P., An Age-based Method for Planning Sclerotomy Placement During Pediatric Vitrectomy: A 12-Year Experience, Trans. Am. Ophthalmol. Soc. vol. 105, p. 86-91 (2007) (available at http://www.ncbi.nlm.nih.gov/pmc/articles/PMC2258105/pdf/1545-6110_v105_p086.pdf).
Randy Pell, Surgical Instruments: Converting from Metal to Plastic, Medical Device & Diagnostic Industry, Oct. 2006, Canon Communications, 2006, available at http://www.mack.com/resource/MDDI_Oct06_RPell.pdf (last visited Oct. 22, 2013).
Rhein Medical, Quick View Ophthalmic Surgical Instruments Available from Rhein Medical, 05-7001 Fine Crescent Fixation Ring, p. 32, Nov. 27, 2012, available at http://www.rheinmedical.com/wp-content/uploads/2012/11/QuickView1248gWEB.pdf.
Rhein Medical, Quick View Ophthalmic Surgical Instruments Available from Rhein Medical, 05-7008 Seibel Gravity Fixation Ring, p. 59, Nov. 27, 2012, available at http://www.rheinmedical.com/wp-content/uploads/2012/11/QuickView1248gWEB.pdf.
U.S. Appl. No. 13/967,133, filed Aug. 14, 2013, Positioning Device for Eye Surgery and Procedures.
U.S. Appl. No. 15/228,500, Positioning Device for Eye Surgery and Procedures.

\* cited by examiner

EYE FIXATION SYSTEM FOR POSTERIOR AND ANTERIOR SEGMENT EYE SURGERY AND PROCEDURES

CROSS-REFERENCE TO RELATED APPLICATIONS

This application claims priority to U.S. provisional patent application Ser. No. 61/682,770, filed Aug. 14, 2012, the contents of which is incorporated herein by reference in its entirety.

BACKGROUND

The recent introduction of small gauge vitrectomy instrumentation in vitreoretinal surgery provides a great opportunity for more efficient, less traumatic and safer surgery. A trocar system is used through which instruments are introduced and exchanged throughout the procedure.

Introduction and removal of the trocars require several instruments and maneuvers that are typically implemented in multiple steps. These include: (a) stabilization of the eye; (b) location of the correct trocar position in pars plana in such a way that the natural lens is not traumatized by the introduction of the trocar or instruments and in such a way as not to introduce the instruments through the retina resulting in tears that can lead to retinal detachment; (c) dragging of the conjunctiva to cause a misalignment of entry points in conjunctiva and sclera; (d) removal of the sharp blade introducing the trocar; (e) positioning of the irrigation cannula; (e) repeating the key steps above three times in the most common three port pars plana vitrectomy surgery.

Completion of these steps is crucial to the initiation of the procedure in a safe and efficient manner. Presently these are performed using multiple instruments that are repeatedly exchanged for the performance of the individual steps and for the performance of each of the three sclerotomies.

SUMMARY

The present invention is for an eye fixation and stabilization system and accurate instrument positioning system which can be utilized for the fixating and stabilizing the eye and locating the accurate position for instruments to be positioned, introduced and manipulated during eye surgery, eye procedures and eye exams. It can be used in anterior segment surgery as exemplified but not limited to cataract surgery and refractive surgery as well as for vitreoretinal procedures and posterior segment surgeries as exemplified by but not limited to vitrectomy and intravitreal injections, providing a universal tool for stabilization, fixation and accurate positioning and manipulation of other instruments.

In one aspect, the invention provides an instrument having a handle, one end of which a swiveling, extended ring is attached. The extended ring includes (a) an internal edge with an internal circumference that approximately coincides with the limbus; (b) an external edge with an external circumference that is about 4 millimeters from the internal edge; (c) four windows at the external edge; and (d) a mark at each windows indicating a position that is about 3.5 millimeters from the internal edge. The extended ring has an inside surface that contacts the eye when the instrument is placed on the eye, the inside surface being roughened for improved contact with the eye thereby allowing the eye to be manipulated.

In some embodiments, the handle of the instrument is attached to the extended ring through two prongs on one end of the handle, each prong being secured to a tab on the internal edge of the extended ring using a pin inserted through the prong and tab.

In another aspect, the invention provides an extended ring that includes (a) an internal edge with an internal circumference that approximately coincides with the limbus; (b) an external edge with an external circumference that is about 4 millimeters from the internal edge; (c) four windows at the external edge; (d) a mark at each window indicating a position that is about 3.5 millimeters from the internal edge; and (e) two tabs on the upper edge of the extended ring to facilitate handling. The extended ring has an inside surface that contacts the eye when the instrument is placed on the eye, the inside surface being roughened for improved contact with the eye thereby allowing the eye to be manipulated.

Thus, in some embodiments, the positioning device is used for eye fixation and stabilization, as well as to assist in accurate instrument positioning, introduction and/or manipulation during eye examinations, surgeries or procedures. In some embodiments, the positioning device can be used in anterior segment surgery such as, for example, cataract surgery and refractive surgery, as well as for vitreoretinal procedures and posterior segment surgeries such as, for example, virectomy and intravitreal injections.

Any feature or combination of features described herein are included within the scope of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION

The general purpose of the present invention is to position and stabilize the eye during various procedure, surgeries and examinations performed on the eye and allow the accurate positioning and manipulation of various instruments while reducing the number of instruments exchanges to a bare minimum.

The instrument can be used for a variety of procedures such as stabilization for cataract, LASIK and other refractive eye surgeries. A novel application of this specific instrument is described in further detail for the case of small gauge vitreoretinal surgery (trans pars plana vitrectomy (TPPV)).

Figure 1:
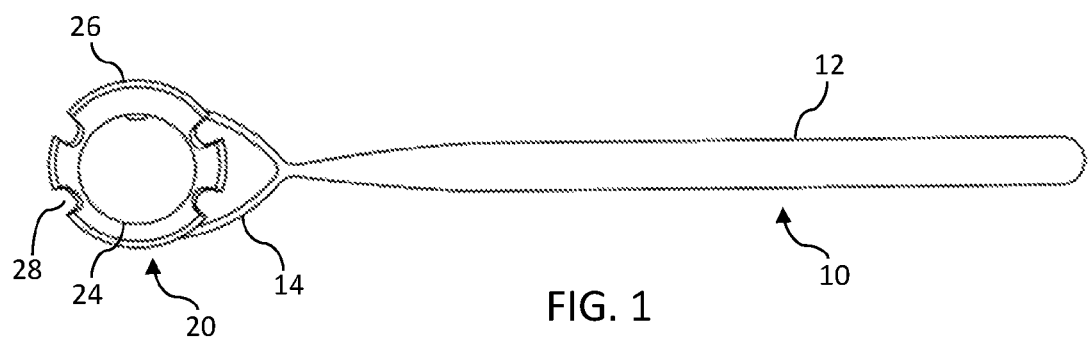
FIG. 1 is a view of instrument 1 from the underside of the swiveling extended ring 20 showing swiveling extended ring 20 attached to one end of handle 10 through two-prong end portion 14.
Figure 2:
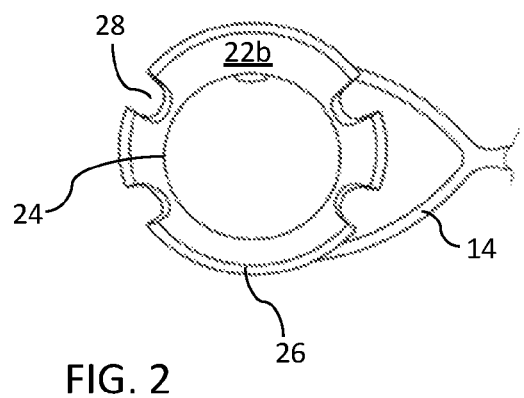
FIG. 2 is an enlarged view of underside 22b of the swiveling extended ring 20 shown in FIG. 1.
Figure 3:
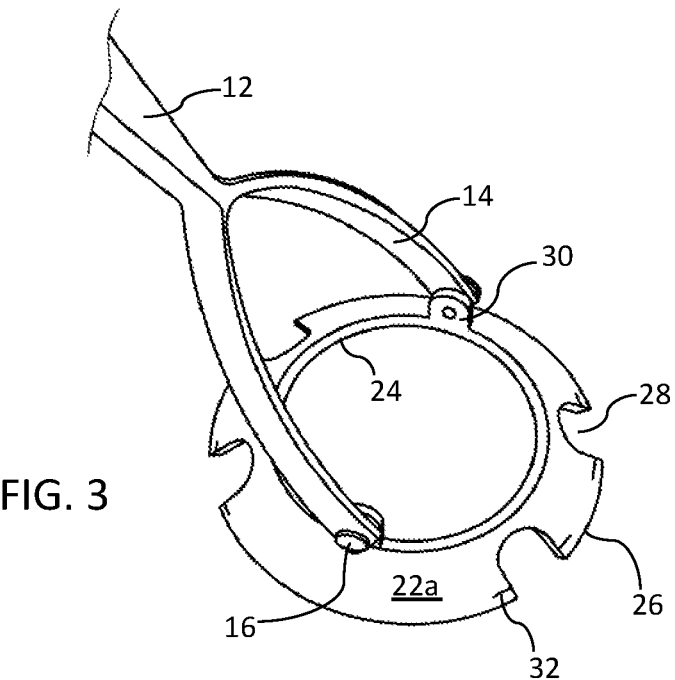
FIG. 3 is an enlarged top view of swiveling extended ring 20 attached to one end of handle 10 through tabs 30, two-prong end portion 14 of handle 10, and pin 16.
Figure 4:
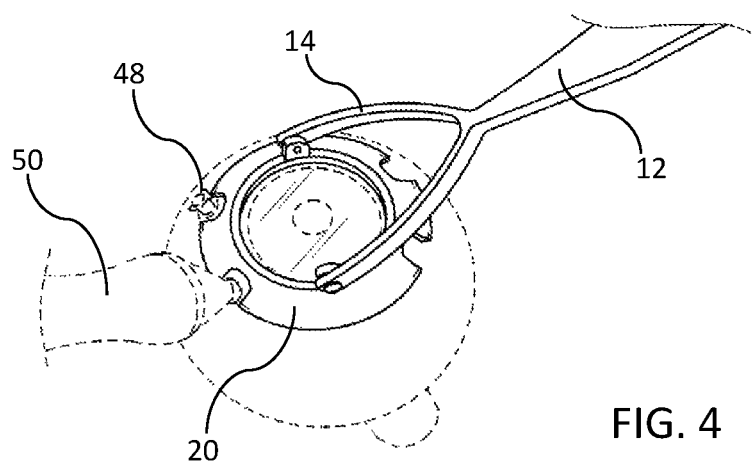
FIG. 4 is a top view of instrument 1 placed on a model of an eye.

The device of the invention is handheld instrument 1 that has a handle 10 at the end of which there is a swiveling extended "ring" 20 (or portion of a ring or arc). Handle 10 has elongated shaft 12 and two-prong end portion 14. The handle is attached to the extended ring 20 through two-prong end portion 14. The central portion of the ring (or portion of a ring or arc) has dimensions commensurate with the diameter of the cornea and is intended to approximately coincide with the limbus. Thus, the central portion has an internal edge 24 (FIG. 1, 2) with an internal circumference approximately coincides with the limbus when the instrument is placed on the eye as shown in FIG. 4. The extended ring has external edge 26 with an external circumference that is larger than internal circumference of internal edge 24 as shown in FIGS. 1 and 2. The external edge is positioned at a distance commensurate with the placement of a trocar in a phakic eye. This distance is often taken to be 4 mm from the limbus. There are four of small window 28 at external edge 26 of the extended ring. The windows angular and radial position allow for the accurate and safe positioning of the trocars. Mark 32 near the window allows for the sometime preferred positioning for a pseudophakic eye. Mark 32 can be placed next to each window as shown in FIG. 3. Often that measurement is taken to be 3.5 mm from the limbus. The size of the windows is also such as to allow the safe introduction of the trocars and removal of the blades and other instruments (e.g. trocar cannula 48 and trocar system 50, FIG. 4), as well as the stabilization of the trocar during the introduction of the infusion cannula without necessitating the use of another instrument. The extended ring inside surface 22b (the one facing the eye) has a roughened surface in order to improve on the grasping ability of the eye and prevents slipping. It also allows full control and manipulation of the globe including rotation around a vertical axis (visual axis) to expose the areas of the eye needed for positioning before and after introduction of the trocars and this even in smaller eyes.

Figure 5:
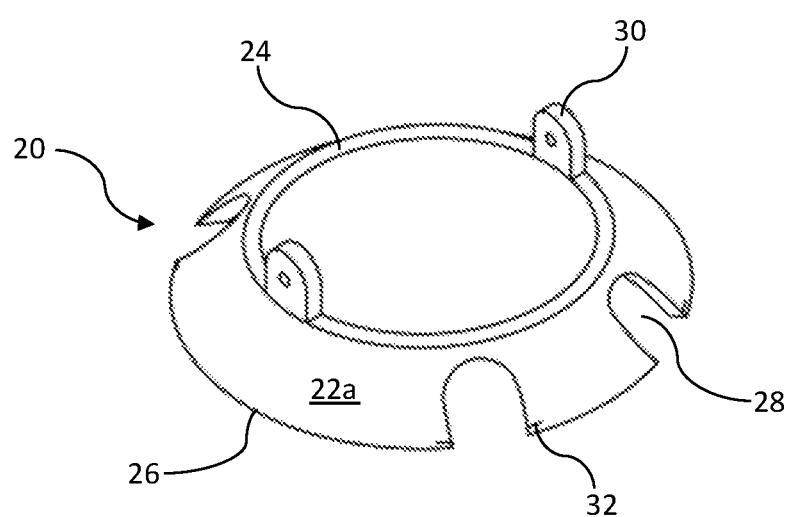
FIG. 5 is a top view of an embodiment of an extended ring of the invention without a handle, in particular, extended ring 20 without attached handle 10.

FIG. 1 illustrates instrument 1 of the invention. Handle 10 includes shaft 12 and two-prong end portion 14. Swivel extended ring 20 includes internal edge 24, external edge 26, inside surface 22b and four of windows 28. FIG. 2 is an enlarged bottom view of one end of instrument 1 showing extended ring 20 with inside surface 22b, internal edge 24, external edge 26, four of windows 28 attached to two-prong end of handle 10. FIG. 3 is an enlarged top view of one end of instrument 1 showing extended ring 20 with outside surface 22a, internal edge 24, external edge 26, four of windows 28 attached to two-prong end portion 14 of handle 10. FIG. 4 illustrates instrument 1 on an eye showing window 28 is of a size sufficient to accommodate instrument 48 and 50. Another embodiment of the invention is shown in FIG. 5, which illustrates an embodiment of the invention in which extended ring 20 with tab 30 is without handle 10.

In the current methods of small gauge vitreoretinal surgery, the introduction of the trocars involve several instruments which are exchanged multiple times each in three cycles, one for each port, for the completion of the safe and effective introduction of the trocar systems. The current instrument is positioned once and plays the role of stabilization, accurate measurement, removal of blade, introduction of the irrigation cannula, without the need for exchange of other instruments as the instrument is placed only once on the eye for the completion of the all cycles of trocar placement.

Procedures for which an instrument of the invention can be used include cataract surgery, refractive surgery including LASIK, anterior segment taps, vitreoretinal surgery and intravitreal injections including anti-VEGF, steroids, antibiotics and any pharmaceutical to be injected intravitreally.

The device of the invention can be made of material consistent with the materials used for similar surgical instruments. It can be made for repeated multiple uses and should be made in such a fashion as to allow for sterilization in the same fashion and along other surgical instruments. It can also be made in a disposable form for single usage to eliminate the need for repeat sterilization and allow for all the advantages typically associated with the use of disposable instruments.

The specific embodiments of the invention described above do not limit the scope of the invention described in the claims.

OTHER EMBODIMENTS OF THE INVENTION

While the invention has been described in conjunction with the detailed description, the foregoing description is intended to illustrate and not limit the scope of the invention, which is defined by the scope of the appended claims. Other aspects, advantages, and modifications are within the scope of the following claims.

The specific methods and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Under no circumstances may the patent application be interpreted to be limited to the specific examples or embodiments or methods specifically disclosed herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as described in the statements of the invention and as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. In addition, the invention has been described broadly and generically herein. Each of the narrower species and subgeneric groupings falling within the generic disclosure also form part of the invention.

What is claimed is:

1. An instrument comprising an elongated handle, one end of which a swiveling, extended ring is attached, the extended ring being adapted to contact an eye when placed on the eye, the extended ring comprising a body having an inside surface and an outside surface extending between an internal edge and an external edge:
   (a) the internal edge comprising an internal circumference that approximately coincides with the limbus of the eye when the extended ring is placed on the eye;
   (b) the external edge comprising an external circumference that is about 4 millimeters from the internal edge;
   (c) the body comprising four windows at the external edge;
   (d) the outside surface comprising a surface mark next to each window indicating a position that is about 3.5 millimeters from the internal edge; and
   (e) the inside surface, which contacts the eye when the extended ring is placed on the eye, being roughened for improved contact with the eye.

2. The instrument of claim 1, wherein the elongated handle is attached to the extended ring through two prongs on the one end of the handle, each prong being secured to a tab on the internal edge of the extended ring using a pin inserted through the prong and tab.

3. An extended ring adapted to contact an eye when placed on the eye, the extended ring comprising a body having an inside surface and an outside surface extending between an internal edge and an external edge:
   (a) the internal edge comprising an internal circumference that approximately coincides with the limbus of the eye when the extended ring is placed on the eye;
   (b) the external edge Hcomprising an external circumference that is about 4 millimeters from the internal edge;
   (c) the body comprising four windows at the external edge and two tabs extending upward from the internal edge;
   (d) the outside surface comprising a surface mark next to each window indicating a position that is about 3.5 millimeters from the internal edge;
   (e) the inside surface, which contacts the eye when the extended ring is placed on the eye, being roughened for improved contact with the eye.

\* \* \* \* \*